United States Patent [19]
Stroppolo et al.

[11] Patent Number: 5,510,385
[45] Date of Patent: Apr. 23, 1996

[54] PHARMACEUTICAL COMPOSITIONS CONTAINING THE SALTS OF S(+)-2-(4-ISOBUTYLPHENYL)PROPIONIC ACID WITH BASIC AMINOACIDS

[75] Inventors: Federico Stroppolo, Pregassona, Switzerland; Daniele Bonadeo, Varese, Italy; Gian F. Fornasini, Milan, Italy; Annibale Gazzaniga, Rescaldina, Italy

[73] Assignee: Zambon Group S.p.A., Vicenza, Italy

[21] Appl. No.: 255,945

[22] Filed: Jun. 7, 1994

[30] Foreign Application Priority Data

Jun. 21, 1993 [IT] Italy ................................ MI93A1324

[51] Int. Cl.⁶ .................................................. A61K 31/205
[52] U.S. Cl. ........................ 514/555; 514/564; 514/565; 514/570
[58] Field of Search ................................ 514/555, 564, 514/565, 570

[56] References Cited

U.S. PATENT DOCUMENTS

| | | | |
|---|---|---|---|
| 4,689,218 | 8/1987 | Gazzaniga et al. | 424/43 |
| 4,834,966 | 5/1989 | Gazzaniga et al. | 424/43 |
| 4,994,604 | 2/1991 | Tung et al. | |
| 5,009,895 | 4/1991 | Lui | 424/465 |
| 5,200,558 | 4/1993 | Kwan | 562/496 |
| 5,260,337 | 11/1993 | Sims et al. | 514/570 |

FOREIGN PATENT DOCUMENTS

| | | |
|---|---|---|
| 2055683 | 5/1992 | Canada . |
| 0424028A2 | 4/1991 | European Pat. Off. . |
| 0486045 | 5/1992 | European Pat. Off. . |
| 0505180 | 9/1992 | European Pat. Off. . |

*Primary Examiner*—Richard L. Raymond
*Attorney, Agent, or Firm*—Oblon, Spivak, McClelland, Maier & Neustadt

[57] ABSTRACT

A pharmaceutical composition for oral use containing the salt of S(+)-2-(4-isobutylphenyl)propionic acid with a basic aminoacid selected between L-arginine and L-lysine is described.

14 Claims, No Drawings

PHARMACEUTICAL COMPOSITIONS CONTAINING THE SALTS OF S(+)-2-(4-ISOBUTYLPHENYL)PROPIONIC ACID WITH BASIC AMINOACIDS

The present invention relates to a pharmaceutical composition for opal use containing a salt of S(+)-2-(4-isobutylphenyl)propionic acid with a basic aminoacid and, mope particularly, it relates to a pharmaceutical composition fop opal use containing the salt of S(+)-2-(4-isobutylphenyl)propionic acid with a basic aminoacid selected between L-arginine and L-lysine.

2-(4-Isobutylphenyl)propionic acid is a known non-steroidal anti-inflammatory drug (Merck Index, XI Ed., no. 4812, page 776) whose International Nonproprietary Name is Ibuprofen.

For the sake of clearness and simplicity, we report here below the terminology which will be used in the present description, unless differently specified, to indicate Ibuprofen, its enantiomeric forms and its salts with basic aminoacids, together with the corresponding meanings:

- Ibuprofen=racemic mixture of 2-(4-isobutylphenyl)propionic acid S(+)-Ibuprofen=(S)-enantiomer of 2-(4-isobutylphenyl)propionic acid
- R(−)-Ibuprofen=(R)-enantiomer of 2-(4-isobutylphenyl)propionic acid
- Ibuprofen salt=salt of Ibuprofen with a basic aminoacid S(+)-Ibuprofen salt=salt of S(+)-Ibuprofen with a basic aminoacid selected between L-arginine and L-lysine
- Ibuprofen arginate=salt of Ibuprofen with L-arginine
- Ibuprofen lysinate=salt of Ibuprofen with L-lysine
- S(+)-Ibuprofen arginate=salt of S(+)-Ibuprofen with L-arginine
- S(+)-Ibuprofen lysinate=salt of S(+)-Ibuprofen with L-lysine.

Ibuprofen is widely used in therapy, for its analgesic, anti-inflammatory and anti-pyretic properties, in the form of racemic mixture that is in the form of a mixture 1:1 of the two enantiomers S(+)-Ibuprofen and R(−)-Ibuprofen.

From some years, it is known that S(+)-Ibuprofen is the pharmacologitally active enantiomer of Ibuprofen.

In the literature, it is also described that the use of S(+)-Ibuprofen allows to obtain some therapeutic advantages in comparison with the administration of an equivalent dose of Ibuprofen. International patent application WO 89/00421 (Sunshine A. and Laska E. M.) describes, for example, that S(+)-Ibuprofen has a faster, and consequently a longer, analgesic effect than Ibuprofen.

Similarly, European patent application no. 424028 (Merck & Co. Inc.) describes that the salts of S(+)-Ibuprofen with basic aminoacids such as L-lysine, L-arginine, L-hystidine, D-lysine, D-arginine and D-hystidine allow to obtain a faster and longer analgesic effect than Ibuprofen, than Ibuprofen salts and than S(+)-Ibuprofen.

In the above cited European patent application no. 424028, the faster and longer analgesic effect is described in particular in the case of the salts of S(+)-Ibuprofen with L-lysine or D-tysine. The cited patent applications suggest that the use of S(+)-Ibuprofen and particularly of its salts with basic aminoacids represents an advantage in the case of the analgesic treatment of moderate pains, such as pains consequent on oral surgery, post-partum uterine cramps and dysmenorrhea, because of the faster onset of the analgesic effect.

Furthermore, the literature suggests that such a therapeutic advantage is particularly noticeable at low analgesic doses.

However, low doses of Ibuprofen, generally lower than or equal to 200 mg, ape not therapeutically useful in the case of the analgesic treatment of severe pains, especially when these ape associated to various inflammatory conditions.

Therefore, there is a strong need of pharmaceutical compositions allowing to efficiently and advantageously treat pathologies which combine moderate and severe pains with more or less severe inflammatory conditions such as, for example, osteoarthrosis and correlated syndromes, degenerative or inflammatory rheumatic diseases, rheumatoid arthritis, ankylosing spondylapthpitis, pepiapticulap and extra-auricular rheumatic diseases.

For the treatment of these particular diseases, which in the most cases need a very long therapy, non-steroidal anti-inflammatory drugs are used at high doses both as lap as the single dose and the daily dose ape concerned.

For example, in the case of Ibuprofen, the therapeutic daily doses are from 600 mg to 1800 mg to be divided into one of more administrations.

We have now found that the salts of S(+)-Ibuprofen with basic amino-acids and, in particular, the salts of S(+)-Ibuprofen with a basic aminoacid selected between L-arginine and L-lysine, show particular therapeutic advantages when administered by opal route at doses higher than 200 mg, expressed as S(+)-Ibuprofen content.

Therefore, object of the present invention is a pharmaceutical composition for opal use containing a salt of S(+)-Ibuprofen with a basic aminoacid selected between L-arginine and L-lysine in an amount, expressed as S(+)-Ibuprofen, higher than 200 mg in admixture with a pharmaceutically acceptable carrier.

Preferably, the amount of S(+)-Ibuprofen salt is from 300 mg to 800 mg, expressed as S(+)-Ibuprofen Still more preferably, the amount of S(+)-Ibuprofen salt is equivalent to 300 mg or 400 mg of S(+)-Ibuprofen.

The pharmaceutical composition for oral use object of the present invention can be in solid or liquid form.

Examples of pharmaceutical compositions in solid form are powders, granulates, tablets and capsules.

Examples of pharmaceutical compositions in liquid form are aqueous solutions, syrups and oral drops.

Dependently from the selected pharmaceutical form, the pharmaceutically acceptable carrier may contain sweetening agents, flavouring agents, diluents, disintegrating agents, lubricating agents and thickening agents.

Specific examples are sweetening agents such as saccharose, sorbitol, mannitol, saccharin and aspartame, flavouring agents such as natural or natural-like flavors, diluents such as sugars and celluloses, disintegrating agents such as cross-linked polyvinylpyrrolidone, sodium bicarbonate and sodium carbonate, lubricants such as magnesium stearate, hydrogenated castor oil, polyethylen glycol, thickening agents such as modified celluloses, polyvinylalcohol and polyvinylpyrrolidone.

Preferably, the pharmaceutical composition object of the present invention is in solid form.

Still more preferably, the pharmaceutical composition object of the present invention is in the form of optionally effervescent granulates or tablets.

The pharmaceutical compositions of the invention are prepared according to conventional techniques.

As already underlined, the composition containing the S(+)-Ibuprofen salt object of the present invention shows further therapeutic advantages which make it different from the pharmaceutical compositions containing a lower dose of active ingredient.

The compositions object of the invention allow to obtain an anticipation of the onset of the pharmacological effect as reported in the literature.

Furthermore, the pharmaceutical compositions object of the invention allow to reach maximum plasma concentration levels of S(+)-Ibuprofen significantly much higher than those reached with a pharmaceutical composition containing an equivalent dose of Ibuprofen.

As reported in Examples 6, 8 and 9, the values of the S(+)-Ibuprofen maximum plasma concentrations obtained after oral administration of a pharmaceutical composition according to the present invention containing an amount of active ingredient corresponding to 400 mg or 300 mg of S(+)-Ibuprofen, as S(+)-Ibuprofen arginate or lysinate, are about 15–20% higher than those obtained after oral administration of an analogous composition containing an amount of active ingredient corresponding to 800 mg or 600 mg, respectively, of Ibuprofen, as Ibuprofen arginate or lysinate.

It is worth underlining that, after oral administration of a composition containing S(+)-Ibuprofen arginate or lysinate, in an amount corresponding to 200 mg of S(+)-Ibuprofen, the obtained values of maximum plasma concentration are substantially equal to those obtained after administration of an equivalent amount of Ibuprofen arginate or lysinate, respectively (see Examples 7 and 10).

In other words, the maximum plasma concentrations of S(+)-Ibuprofen obtained after administration of 200 mg of S(+)-Ibuprofen in the form of arginine or lysine salt are the same as those obtained by measuring the S(+)-Ibuprofen maximum plasma concentrations after administration of 400 mg of racemic Ibuprofen in the form of arginine or lysine salt.

On the contrary, the levels of S(+)-Ibuprofen maximum plasma concentrations obtained after administration of 300 mg or 400 mg of S(+)-Ibuprofen in the form of arginine or lysine salt are significantly higher than those obtained by measuring the S(+)-Ibuprofen maximum plasma concentration after administration of 600 mg or 800 mg respectively of racemic Ibuprofen in the form of arginine or lysine salt.

This means that the pharmacological effect of the S(+)-Ibuprofen salt, when orally administered at doses higher than 200 mg, expressed as S(+)-Ibuprofen content, is significantly higher than that obtained with an equivalent amount of S(+)-Ibuprofen in the form of the corresponding Ibuprofen salt.

The effect of the compositions object of the present invention was evaluated also in a double blind, randomized study carried out on patients treated with a single dose.

A group of patients was treated with an aqueous solution containing 400 mg of S(+)-Ibuprofen, as S(+)-Ibuprofen arginate, and a second group of patients was treated with an aqueous solution containing 800 mg of Ibuprofen, as Ibuprofen arginate.

The patients suffered from acute or moderate pains consequent on stomatologic surgery (dental extraction).

The rate of onset of the analgesic effect and its efficacy were evaluated by considering the pain intensity and the degree of pain attenuation after 0.5, 1, 1.5, 2, 3, 4, 5 and 6 hours after the administration and by timing the moment of pain disappearance. The obtained results showed a significant improvement of the therapeutic advantages obtained with the administration of a composition according to the present invention with respect to those obtained with the administration of the comparison pharmaceutical composition.

In this regard, it is important to insist on the fact that the improved effect is peculiar to the compositions containing an S(+)-Ibuprofen salt according to the present invention, that is compositions with an S(+)-Ibuprofen content higher than 200 mg; known pharmaceutical compositions containing amounts of S(+)-Ibuprofen, in the form of a salt, lower than or equal to 200 mg do not show such an improved effect.

From a practical point of view, this allows to significantly decrease the doses to be administered to patients in need of therapies with high doses while maintaining the same therapeutic effect, with a consequent lower risk of side effects and toxicity.

It is evident how this represents a remarkable therapeutic advantage mainly as far as therapies requiring the administration of high doses of active ingredient, repeated more times during the day and for prolonged time periods are concerned.

In order to better illustrate the present invention the following examples are now given.

EXAMPLE 1

Preparation of a granulate containing S(+)-Ibuprofen arginate

S(+)-Ibuprofen arginate (738 g) was sieved and put in a mixer. Saccharose (2162 g) and flavour (100 g) were added. After mixing, the granulate was shared into sachets (3 g each) so that the content of S(+)-Ibuprofen per sachet was 400 mg. Alternatively, the granulate was shared into sachets containing 1.5 g or 2.25 g so that the content of S(+)-Ibuprofen per sachet was 300 mg.

By working in the same way, sachets containing 1.5 g corresponding to 200 mg of S(+)-Ibuprofen were prepared as reference.

EXAMPLE 2

Preparation of a reference granulate containing Ibuprofen arginate

Ibuprofen arginate (1476 g) was sieved and put in a mixer. Saccharose (1324 g) and flavour (100 g) were added. After mixing, the granulate was shared into sachets (3 g each) so that the content of Ibuprofen per sachet was 800 mg. Alternatively, the granulate was shared into sachets each containing 1.5 g or 2.25 g so that the content of Ibuprofen per sachet was 400 mg or 600 mg respectively.

EXAMPLE 3

Preparation of tablets containing S(+)-Ibuprofen arginate

S(+)-Ibuprofen arginate (738 g) was sieved and put in a mixer with sodium bicarbonate (300 g) cross-linked polyvinylpyrrolidone (60 g) and magnesium stearate (8 g).

After mixing, the granulate was compressed into tablets each weighing 1106 mg so that each tablet contained 400 mg of S(+)-Ibuprofen.

EXAMPLE 4

Preparation of a granulate containing S(+)-Ibuprofen lysinate

By working as described in Example 1 but substituting S(+)-ibuprofen arginate with an equivalent amount of S(+)-Ibuprofen lysinate, sachets containing an amount of S(+)-Ibuprofen corresponding to 400 mg or 300 mg and reference sachets containing an amount of S(+)-Ibuprofen corresponding to 200 mg were prepared.

EXAMPLE 5

Preparation of a reference granulate containing Ibuprofen lysinate

By working as described in Example 2 but substituting Ibuprofen arginate with an equivalent amount of Ibuprofen lysinate, sachets containing an amount of Ibuprofen corresponding to 800 mg, 400 mg or 600 mg were prepared.

EXAMPLE 6

Comparison between S(+)-Ibuprofen arginate and Ibuprofen arginate (400 mg versus 800)

Aqueous solutions (100 ml) of a granulate containing 400 mg of S(+)-Ibuprofen as S(+)-Ibuprofen arginate (Preparation A-1), prepared as described in Example 1, and aqueous solutions (100 ml) of a granulate containing 800 mg of Ibuprofen as Ibuprofen arginate (Preparation B-1), prepared as described in Example 2, were administered in a single oral dose to 7 subjects with an average age of 35.2 years.

Each subject was apparently healthy, especially as lap as the Renal, hepatic and hematopoietic functions were concerned.

For the trial, a cross-over design was adopted: each subject received both preparations in two treatment sessions carried out in two different weeks randomizing the order of the administration. During each of the two sessions, basal samples of venous blood were withdrawn in the morning to each subject in fasting conditions, before administering Preparation A-1 or Preparation B-1.

Further, samples of venous blood were withdrawn at 5, 10, 15, 30, 45, 60, 90, 120, 240 and 480 minutes after the treatment. Plasma was then prepared by centrifugation and preserved at −20° C. until the analysis.

The analytical determination of the active ingredient in the plasma samples was carried out by HPLC method as described hereinafter. Chromatographic conditions:

Apparatus: JASCO BIP-1 with U.V. detector UVI DEC-100 v

Column: Chiral AGP, 100×4.0 mm, 5 µm (Chron Tech) with a precolumn Chiral AGP 10×3.0 mm (Chron Tech)

Mobile phase: 0.001M N,N-dimethyloctylamine in 0.02N sodium hydrogen phosphate:acetonitrile=99:1, pH 6.5 with NaOH 6M Flow: 1.2 ml/min Wavelength: 230 nm Internal standard: a solution of propyl p.hydroxybenzoate in acetonitrile and phosphate buffer 0.01M pH 7.4.

HCl 3N (150 µl), internal standard solution (50 µl) and phosphate buffer 0.01M pH 7.4 (31.25 µl) were added to plasma (250 µl).

Cyclohexane (5 ml) was added to the solution and, after mixing for 15 minutes and centrifugation at 3500 rpm, the upper phase was separated (3 ml) and the extraction was repeated.

After evaporation of the solvent, the residue was dissolved in phosphate buffer 0.01M pH 7.4 (250 µl).

The solution (50 µl) was injected into the chromatograph.

Under the described operative conditions the retention times (RT) are the following:

| | |
|---|---|
| R(−)-Ibuprofen | RT = 3.5 minutes |
| S(+)-Ibuprofen | RT = 4.8 minutes |
| Internal standard | RT = 10.2 minutes |

The obtained results are reported in the following table 1.

TABLE 1

Mean plasma concentrations of S(+)-Ibuprofen after oral treatment with a solution (100 ml) obtained by dissolution of a sachet containing 400 mg of S(+)-Ibuprofen, in the form of S(+)-Ibuprofen arginate (treatment A-1), according to the present invention, and after oral treatment with a solution (100 ml) obtained by dissolution of a sachet containing 800 mg of Ibuprofen, in the form of Ibuprofen arginate (treatment B-1).

| | S(+)-Ibuprofen plasma concentrations (µg/ml) | |
|---|---|---|
| Sampling times (minutes) | Treatment A-1 | Treatment B-1 |
| 0 | 0 | 0 |
| 5 | 19.09 | 13.65 |
| 10 | 32.35 | 25.83 |
| 15 | 34.40 | 28.63 |
| 30 | 35.11 | 28.91 |
| 45 | 31.61 | 31.41 |
| 60 | 30.50 | 27.75 |
| 90 | 25.30 | 23.67 |
| 120 | 18.16 | 18.91 |
| 240 | 6.90 | 10.80 |
| 480 | 2.41 | 2.74 |

Bioavailability parameters

The following parameters were calculated:

the area under curve of S(+)-Ibuprofen plasma concentration from time "zero" to time 480 minutes ($AUC_{obs} = AUC_{o \rightarrow 480}$), expressed as $\mu g \times min \times ml^{-1}$, was calculated according to the trarezoidal method (gibaldi M. and Perrier D., "Pharmacokinetics", pages 293–296, Marcel Dekker Inc., New York 1975).

the area under curve of S(+)-Ibuprofen plasma concentration from time "zero" to "infinite" ($AUC_{tot}$) was calculated by the following formula: $AUC_{tot} = AUC_{o \rightarrow 480} + AUC_{480 \rightarrow}$ wherein $AUC_{480 \rightarrow}$ =concentration at 480 minutes/$K_e$. and $K_e$=elimination constant mean peak time ($t_{max}$), expressed as minutes, was obtained from the average of each peak time the mean peak of maximum plasma concentration ($C_{max}$), expressed as µg/ml, was calculated by the average of each concentration peak value.

The values of the bioavailability parameters are reported in the following table 2.

TABLE 2

Mean values of the bioavailability parameters obtained after oral treatment with preparation A-1, containing 400 mg of S(+)-Ibuprofen (treatment A-1) and after oral treatment with preparation B-1, containing 800 mg of Ibuprofen (treatment B-1).

| Bioavailability parameters | Treatment A-1 | Treatment B-1 |
|---|---|---|
| $AUC_{obs}$ (µg × min × ml$^{-1}$) | 6072 | 6141 |
| $AUC_{tot}$ (µg × min × ml$^{-1}$) | 5662 | 6749 |
| $t_{max}$ (min) | 32.5 | 35.0 |
| $C_{max}$ (µg/ml) | 40.4 | 34.3(*) |

(*)the $C_{max}$ value reached with treatment A-1 resulted to be significantly higher than that reached with treatment B-1.

The pharmacokinetic data clearly show that S(+)-Ibuprofen derived from treatment A-1 (administration of a pharmaceutical composition according to the present invention) was absorbed more rapidly, mainly during the first minutes after the administration, than the S(+)-Ibuprofen deriving from treatment B-1 and, furthermore, it reached plasma concentrations ($C_{max}$) significantly much higher than the concentrations obtained with the reference treatment (treatment B-1).

EXAMPLE 7

Comparison between S(+)-Ibuprofen arginate and Ibuprofen arginate (200 mR versus 400 mg)

The experimental design described in Example 6 was repeated by administering aqueous solutions (100 ml) of a granulate containing 200 mg of S(+)-Ibuprofen as S(+)-Ibuprofen arginate (Preparation R-1), prepared as described in Example 1, and aqueous solutions (100 ml) of a granulate containing 400 mg of Ibuprofen as Ibuprofen arginate (Preparation R-2), prepared as described in Example 2. The values of S(+)-Ibuprofen plasma concentration obtained after oral administration of Preparation R-1 (Treatment R-1) and after oral administration of Preparation R-2 (Treatment R-2) are reported in the following table 3.

TABLE 3

Mean plasma concentrations of S(+)-Ibuprofen after oral treatment with Preparation R-1, containing 200 mg of S(+)-Ibuprofen in the form of S(+)-Ibuprofen arginate (treatment R-1) and after oral treatment with Preparation R-2, containing 400 mg of Ibuprofen in the form of Ibuprofen arginate (treatment R-2).

| Sampling times (minutes) | S(+)-Ibuprofen plasma concentrations (µg/ml) | |
|---|---|---|
| | Treatment R-1 | Treatment R-2 |
| 0 | 0 | 0 |
| 5 | 10.26 | 8.92 |
| 10 | 18.15 | 16.89 |
| 15 | 21.03 | 17.87 |
| 30 | 20.72 | 18.29 |
| 45 | 18.07 | 18.01 |
| 60 | 15.52 | 16.07 |
| 90 | 12.47 | 13.46 |
| 120 | 9.82 | 11.57 |
| 240 | 3.94 | 4.52 |
| 480 | 1.07 | 1.69 |

The values of the bioavailability parameters are reported in the following table 4.

TABLE 4

Mean values of the bioavailability parameters obtained after oral treatment with preparation R-1, containing 200 mg of S(+)-Ibuprofen (treatment R-1) and after oral treatment with preparation R-2, containing 400 mg of Ibuprofen (treatment R-2).

| Bioavailability parameters | Treatment R-1 | Treatment R-2 |
|---|---|---|
| $AUC_{obs}$ (µg × min × ml$^{-1}$) | 3249 | 3490 |
| $AUC_{tot}$ (µg × min × ml$^{-1}$) | 3420 | 3772 |
| $t_{max}$ (min) | 22.5 | 27.5 |
| $C_{max}$ (µg/ml) | 23.09 | 21.55(*) |

(*)the $C_{max}$ value reached with treatment R-1 resulted to be not significantly different from that reached with treatment R-2.

Also the other pharmacokinetic parameters referred to S(+)-Ibuprofen obtained with treatment R-1 do not significantly differ from those obtained with treatment R-2.

A trend towards an anticipated absorption of S(+)-Ibuprofen derived from treatment R-1 in comparison with that derived from treatment R-2 can be noted.

EXAMPLE 8

Comparison between S(+)-Ibuprofen lysinate and Ibuprofen lysinate (400 mg versus 800 mg)

The experimental design described in Example 6 was repeated by administering aqueous solutions (100 ml) of a granulate containing 400 mg of S(+)-ibuprofen as S(+)-Ibuprofen lysinate (Preparation A-2), prepared as described in Example 4, and aqueous solutions (100 ml) of a granulate containing 800 mg of Ibuprofen as Ibuprofen lysinate (Preparation B-2), prepared as described in Example 5. The values of S(+)-Ibuprofen plasma concentration obtained after oral administration of Preparation A-2 (Treatment A-2) and after oral administration of Preparation B-2 (Treatment B-2) are reported in the following table 5.

TABLE 5

Mean Plasma concentrations of S(+)-Ibuprofen after oral treatment with Preparation A-2, containing 400 mg of S(+)-Ibuprofen in the form of S(+)-Ibuprofen lysinate (treatment A-2) and after oral treatment with Preparation B-2, containing 800 mg of Iguprofen in the form of Ibuprofen lysinate (treatment B-2).

| Sampling times (minutes) | S(+)-Ibuprofen plasma concentrations (µg/ml) | |
|---|---|---|
| | Treatment A-2 | Treatment B-2 |
| 0 | 0 | 0 |
| 5 | 18.5 | 10.1 |
| 10 | 33.4 | 22.4 |
| 15 | 35.6 | 25.1 |
| 30 | 37.3 | 30.0 |
| 45 | 32.5 | 31.4 |
| 60 | 30.0 | 27.8 |
| 90 | 25.2 | 26.4 |
| 120 | 19.0 | 23.3 |
| 240 | 7.33 | 12.6 |
| 480 | 3.09 | 4.93 |

The values of the bioavailability parameters are reported in the following table 6.

TABLE 6

Mean values of the bioavailability parameters obtained after oral treatment with preparation A-2, containing 400 mg of S(+)-Ibuprofen (treatment A-2) and after oral treatment with preparation B-2, containing 800 mg of Ibuprofen (treatment B-2).

| Bioavailability parameters | Treatment A-2 | Treatment B-2 |
|---|---|---|
| $AUC_{obs}$ (µg × min × ml$^{-1}$) | 6180 | 7200 |
| $AUC_{tot}$ (µg × min × ml$^{-1}$) | 6734 | 8295 |
| $t_{max}$ (min) | 32.0 | 45.5 |
| $C_{max}$ (µg/ml) | 37.8 | 30.7(*) |

(*)the $C_{max}$ value reached with treatment A-2 resulted to be significantly higher than that reached with treatment B-2.

The pharmacokinetic data clearly show that S(+)-Ibuprofen derived from treatment A-2 (administration of a pharmaceutical composition according to the present invention) was absorbed more rapidly, mainly during the first minutes after the administration, than the S(+)-Ibuprofen deriving from treatment B-2 and, furthermore, it reached plasma concentrations ($C_{max}$) significantly much higher than the concentrations obtained with the reference treatment (treatment B-2).

EXAMPLE 9

Comparison between S(+)-Ibuprofen lysinate and Ibuprofen lysinate (300 mg versus 600 mg)

The experimental design described in Example 6 was repeated by administering aqueous solutions (100 ml) of a granulate containing 300 mg of S(+)-Ibuprofen as S(+)-Ibuprofen lysinate (Preparation A-3), prepared as described in Example 4, and aqueous solutions (100 ml) of a granulate containing 600 mg of Ibuprofen as Ibuprofen lysinate (Preparation B-3), prepared as described in Example 5.

The values of S(+)-Ibuprofen plasma concentration obtained after opal administration of Preparation A-3 (Treatment A-3) and after oral administration of Preparation B-3 (Treatment B-3) are reported in the following table 7.

TABLE 7

Mean plasma concentrations of S(+)-Ibuprofen after oral treatment with Preparation A-3, containing 300 mg of S(+)-Ibuprofen in the form of S(+)-Ibuprofen lysinate (treatment A-3) and after oral treatment with Preparation B-3, containing 600 mg of Ibuprofen in the form of Ibuprofen lysinate (treatment B-3).

| Sampling times (minutes) | S(+)-Ibuprofen plasma concentrations ($\mu$g/ml) | |
|---|---|---|
| | Treatment A-3 | Treatment B-3 |
| 0 | 0 | 0 |
| 5 | 13.9 | 8.0 |
| 10 | 25.1 | 19.6 |
| 15 | 26.7 | 20.3 |
| 30 | 29.0 | 21.2 |
| 45 | 24.4 | 22.6 |
| 60 | 21.5 | 20.8 |
| 90 | 17.0 | 19.0 |
| 120 | 14.3 | 17.5 |
| 240 | 6.72 | 8.64 |
| 480 | 2.15 | 3.71 |

The values of the bioavailability parameters are reported in the following table 8.

TABLE 8

Mean values of the bioavailability parameters obtained after oral treatment with preparation A-3, containing 300 mg of S(+)-Ibuprofen (treatment A-3) and after oral treatment with preparation B-3, containing 600 mg of Ibuprofen (treatment B-3).

| Bioavailability parameters | Treatment A-3 | Treatment B-3 |
|---|---|---|
| $AUC_{obs}$ ($\mu$g × min × ml$^{-1}$) | 4615 | 5250 |
| $AUC_{tot}$ ($\mu$g × min × ml$^{-1}$) | 4703 | 6180 |
| $t_{max}$ (min) | 28.3 | 44.6 |
| $C_{max}$ ($\mu$g/ml) | 31.0 | 24.2(*) |

(*)the $C_{max}$ value reached with treatment A-3 resulted to be significantly higher than that reached with treatment B-3.

The pharmacokinetic data clearly show that S(+)-Ibuprofen derived from treatment A-3 (administration of a pharmaceutical composition according to the present invention) was absorbed more rapidly, mainly during the first minutes after the administration, than the S(+)-Ibuprofen deriving from treatment B-3 and, furthermore, it reached plasma concentrations ($C_{max}$) significantly much higher than the concentrations obtained with the reference treatment (treatment B-3).

EXAMPLE 10

Comparison between S(+)-Ibuprofen lysinate and Ibuprofen lysinate (200 mg versus 400 mg)

The experimental design described in Example 6 was repeated by administering aqueous solutions (100 ml) of a granulate containing 200 mg of S(+)-Ibuprofen as S(+)-Ibuprofen lysinate (Preparation R-3), prepared as described in Example 4 and aqueous solutions (100 ml) of a granulate containing 400 mg of Ibuprofen as Ibuprofen lysinate (Preparation R-4), prepared as described in Example 5. The values of S(+)-Ibuprofen plasma concentration obtained after opal administration of Preparation R-3 (Treatment R-3) and after opal administration of Preparation R-4 (Treatment R-4) are reported in the following table 9.

TABLE 9

Mean plasma concentrations of S(+)-Ibuprofen after oral treatment with Preparation R-3, containing 200 mg of S(+)-Ibuprofen in the form of S(+)-Ibuprofen lysinate (treatment R-3) and after oral treatment with Preparation R-4, containing 400 mg of Ibuprofen in the form of Ibuprofen lysinate (treatment R-4).

| Sampling times (minutes) | S(+)-Ibuprofen plasma concentrations ($\mu$g/ml) | |
|---|---|---|
| | Treatment R-3 | Treatment R-4 |
| 0 | 0 | 0 |
| 5 | 11.0 | 8.13 |
| 10 | 17.9 | 16.0 |
| 15 | 21.2 | 20.3 |
| 30 | 19.8 | 20.8 |
| 45 | 17.5 | 17.7 |
| 60 | 15.8 | 17.3 |
| 90 | 11.9 | 14.3 |
| 120 | 10.0 | 12.1 |
| 240 | 5.31 | 7.03 |
| 480 | 1.90 | 2.25 |

The values of the bioavailability parameters are reported in the following table 10.

TABLE 10

Mean values of the bioavailability parameters obtained after oral treatment with preparation R-3, containing 200 mg of S(+)-Ibuprofen (treatment R-3) and after oral treatment with preparation R-4, containing 400 mg of Ibuprofen (treatment R-4).

| Bioavailability parameters | Treatment R-3 | Treatment R-4 |
|---|---|---|
| $AUC_{obs}$ ($\mu$g × min × ml$^{-1}$) | 3410 | 4074 |
| $AUC_{tot}$ ($\mu$g × min × ml$^{-1}$) | 3698 | 4560 |
| $t_{max}$ (min) | 14.8 | 28.5 |
| $C_{max}$ ($\mu$g/ml) | 22.3 | 21.0(*) |

(*)the $C_{max}$ value reached with treatment R-3 resulted to be not significantly different from that reached with treatment R-4.

What we claim is:

1. A pharmaceutical composition comprising a salt of S(+)-Ibuprofen with a basic aminoacid selected between L-arginine and L-lysine in an amount, expressed as S(+)-Ibuprofen, of from 300 to 800 mg in admixture with a pharmaceutically acceptable carrier.

2. A pharmaceutical composition according to claim 1 wherein amount of S(+)-Ibuprofen salt is from 300 mg to 400 mg, expressed as S(+)-Ibuprofen.

3. A pharmaceutical composition according to claim 1 wherein the amount of the S(+)-Ibuprofen salt corresponds to 400 mg of S(+)-Ibuprofen.

4. A pharmaceutical composition according to claim 1 wherein the S(+)-Ibuprofen salt is S(+)-Ibuprofen arginate.

5. A pharmaceutical composition according to claim 1 wherein the S(+)-Ibuprofen salt is S(+)-Ibuprofen lysinate.

6. The pharmaceutical composition as claimed in claim 1, consisting essentially of said salt of S(+)-Ibuprofen, with said basic aminoacid and said pharmaceutically acceptable carrier.

7. The pharmaceutical composition as claimed in claim 2, consisting essentially of said salt of S(+)-Ibuprofen, with said basic aminoacid and said pharmaceutically acceptable carrier.

8. The pharmaceutical composition as claimed in claim 3, consisting essentially of said salt of S(+)-Ibuprofen, with said basic aminoacid and said pharmaceutically acceptable carrier.

9. The pharmaceutical composition as claimed in claim 4, consisting essentially of said salt of S(+)-Ibuprofen salt, and said pharmaceutically acceptable carrier.

10. The pharmaceutical composition as claimed in claim 5, consisting essentially of said salt of S(+)-Ibuprofen, and said pharmaceutically acceptable carrier.

11. A method for the treatment of pathologies which combine moderate or severe pain with inflammatory conditions comprising the administration of a pharmaceutical composition comprising a salt of S(+)-Ibuprofen with a basic aminoacid selected between L-arginine and L-lysine in an amount., expressed as S(+)-Ibuprofen, of from 300 to 800 mg in admixture with a pharmaceutically acceptable carrier.

12. A method for the treatment of patients in need of therapies with high doses of an analgesic and antiinflammatory agent comprising the administration of a pharmaceutical composition comprising a salt of S(+)-Ibuprofen with a basic aminoacid selected between L-arginine and L-lysine in an amount, expressed as S(+)-Ibuprofen, of 300–400 mg in admixture with a pharmaceutically acceptable carrier.

13. The method as claimed in claim 11, wherein said pharmaceutical composition consists essentially of said salt of S(+)-Ibuprofen, with said basic aminoacid and said pharmaceutically acceptable carrier.

14. The method as claimed in claim 12, wherein said pharmaceutical composition consists essentially of said salt of S(+)-Ibuprofen, with said basic aminoacid and said pharmaceutically acceptable carrier.

* * * * *